United States Patent
Baroni et al.

(10) Patent No.: US 7,858,824 B2
(45) Date of Patent: Dec. 28, 2010

(54) ARALKYLTETRAHYDROPYRIDINES, THEIR PREPARATION AND PHARMACEUTICAL COMPOSITIONS CONTAINING THEM

(75) Inventors: Marco Baroni, Vanzago (IT); Bernard Bourrie, Saint-Gely-Du Fesc (FR); Rosanna Cardamone, Como (IT); Pierre Casellas, Montpellier (FR)

(73) Assignee: sanofi-aventis, Paris (FR)

( * ) Notice: Subject to any disclaimer, the term of this patent is extended or adjusted under 35 U.S.C. 154(b) by 335 days.

(21) Appl. No.: 11/958,476

(22) Filed: Dec. 18, 2007

(65) Prior Publication Data
US 2008/0097117 A1  Apr. 24, 2008

Related U.S. Application Data

(63) Continuation of application No. 10/492,770, filed as application No. PCT/FR02/03508 on Oct. 14, 2002, now Pat. No. 7,326,723.

(30) Foreign Application Priority Data
Oct. 18, 2001  (FR) .................................. 01 13469

(51) Int. Cl.
*C07C 61/29*  (2006.01)
(52) U.S. Cl. ...................... 562/403; 562/400
(58) Field of Classification Search .................. None
See application file for complete search history.

(56) References Cited

U.S. PATENT DOCUMENTS 5,281,606 A  1/1994  Guzzi et al.

6,070,784 A * 6/2000  Holt et al. ................ 228/112.1

FOREIGN PATENT DOCUMENTS

EP   447116 A1 * 9/1991
WO   WO 96/01267 A1 * 1/1996
WO   WO 01/49679    7/2001

OTHER PUBLICATIONS

West, Anthony R., Solid State Chemistry and its Applications, Wiley, New York, 1988, pp. 358 & 365.*
Giardina et al, Journal of Medicinal Chemistry (1994), 37(21), pp. 3482-3491.*
Bourrie et al, The neuroprotective agent SR57746A abrogats experimental autoimmune encephalomyelitis and impairs associated blood-brain barrier disruption: Implications for multiple sclerosis treatment, Proc. Natl. Acad. Sci. USA, vol. 96, No. 22, 1999, pp. 12855-128859.
Ochiai et al, Syntheses of Alkylphenanthrenes III, Pharmaceutical Bulletin (1957) vol. 5. pp. 108-112.

* cited by examiner

*Primary Examiner*—Zinna N Davis
(74) *Attorney, Agent, or Firm*—Serena Farquharson-Torres

(57) ABSTRACT

The present invention relates to compounds of formula (III°):

(III°)

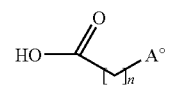

in which n is an integer from 1 to 5; A° represents a partially saturated carbonaceous bi- or tricycle; it also relates to their salts, solvates, N-oxides, the pharmaceutical compositions containing them, a method for their preparation and synthesis intermediates in this method.

2 Claims, No Drawings

ARALKYLTETRAHYDROPYRIDINES, THEIR PREPARATION AND PHARMACEUTICAL COMPOSITIONS CONTAINING THEM

This application is a Continuation of application Ser. No. 10/492,770, filed Apr. 16, 2004, now U.S. Pat. No. 7,326,723, which is the National Stage of International Application No. PCT/FR02/03508, filed Oct. 14, 2002.

FIELD OF THE INVENTION

The present invention relates to novel aralkyltetrahydropyridines, the pharmaceutical compositions containing them, a method for their preparation and synthesis intermediates in this method.

BACKGROUND OF THE INVENTION

EP 0 458 697 describes naphthylalkyltetrahydropyridine derivatives having an intestinal motility modulating activity.

Bourrié et al. (Proc. Natl. Acad. Sci. 1999, 96(22):12855-12859) have described the activity of a compound called SR 57746 (1-(2-naphth-2-ylethyl)-4-(3-trifluoromethyl)-1,2,3,6-tetrahydropyridine) in an experimental autoimmune encephalomyelitis (EAE) model and in the modulation of TNF-alpha (Tumor Necrosis Factor).

It has now been found that some tetrahydropyridines, substituted with a partially saturated aralkyl radical, possess a potent activity on the modulation of TNF-alpha.

TNF-alpha is a cytokine which has recently aroused interest as a mediator of immunity, of inflammation, of cell proliferation, of fibrosis, etc. This mediator is present in abundance in inflamed synovial tissue and exercises an important role in the pathogenesis of autoimmunity (Annu. Rep. Med. Chem., 1997, 32:241-250).

SUMMARY OF THE INVENTION

Thus, the present invention relates, according to one of its aspects, to aralkyltetrahydropyridines of formula (I):

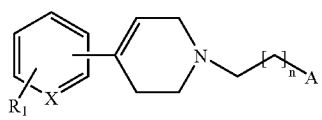

(I)

in which
x represents N or CH;
$R_1$ represents a hydrogen or halogen atom or a $CF_3$ group;
n is an integer from 1 to 5;
A represents a group of formula (a) to (d):

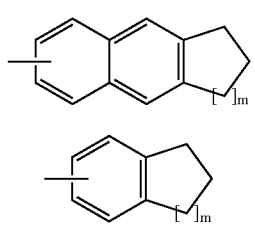

(a)

(b)

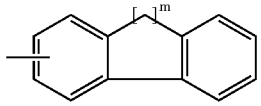

(c)

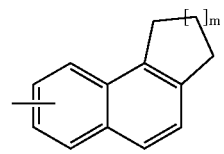

(d)

in which m is 1 or 2;
and their salts or solvates and their N-oxides.

DETAILED DESCRIPTION OF THE INVENTION

In the present description, the term "halogen" denotes an atom chosen from chlorine, bromine, iodine and fluorine.

Preferred compounds are those where n is 1.

Other preferred compounds are those where $R_1$ is a $CF_3$ group.

Other preferred compounds are those where X is CH and $R_1$ is at the 3-position of the benzene.

Other preferred compounds are those where X is CH and $R_1$ is a $CF_3$ group.

Other preferred compounds are those where X is N and pyridine is substituted at the 2,6-positions.

The salts of the compounds of formula (I) according to the present invention comprise both the addition salts with pharmaceutically acceptable inorganic or organic acids such as the hydrochloride, hydrobromide, sulfate, hydrogen sulfate, dihydrogen phosphate, citrate, maleate, tartrate, fumarate, gluconate, methanesulfonate, 2-naphthalenesulfonate, etc., and the addition salts which allow a suitable separation or crystallization of the compounds of formula (I), such as the picrate or oxalate, or the addition salts with optically active acids, for example camphorsulfonic acids and mandelic acids or substituted mandelic acids.

According to the present invention, the compounds of formula (I) may exist as N-oxide derivatives, in particular they may bear an N-oxide group on the tetrahydropyridine.

The compounds of formula (I) can be synthesized by a method which involves (a) reacting the compound of formula (II):

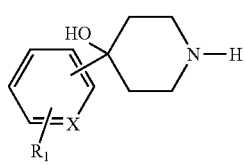

(II)

in which $R_1$ is as defined above, with the acid of formula (III) or one of its functional derivatives:

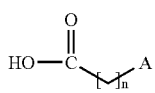

in which n and A are as defined above, (b) reducing the carbonyl group of the compound of formula (IV) thus obtained:

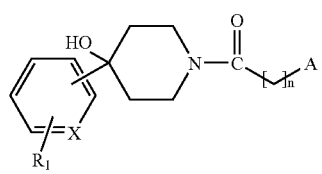

(c) dehydrating the intermediate piperidinol of formula (V) thus obtained

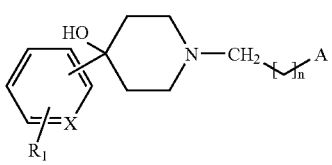

(d) isolating the compound of formula (I) thus obtained and optionally converting it to one of its salts or solvates or to its N-oxide derivatives.

The reaction of step (a) can be suitably carried out in an organic solvent at a temperature of between −10° C. and the reflux temperature of the reaction mixture.

It may be preferable to carry out the reaction at cold temperature when it is exothermic, as in the case where the chloride is used as functional derivative of the acid of formula (III).

As compound of formula (III), it is possible to use either the free acid, optionally activated (for example with BOP, namely tri(dimethylamino)benzotriazol-1-yloxyphosphonium hexafluorophosphate), or one of its functional derivatives such as, for example, an anhydride, a mixed anhydride, an active ester or an acid halide, preferably the bromide. Among the active esters, p-nitrophenyl ester is particularly preferred, but methoxyphenyl, trityl and benzhydryl esters, and the like, are also suitable.

As reaction solvent, a halogenated solvent such as methylene chloride, dichloroethane, 1,1,1-trichloroethane, chloroform or the like, is preferably used, but other organic solvents compatible with the reagents used, for example dioxane, tetrahydrofuran or a hydrocarbon such as hexane, may also be used.

The reaction may be suitably carried out in the presence of a proton acceptor, for example an alkali metal carbonate or a tertiary amine such as triethylamine.

The reduction of step (b) may be suitably carried out by appropriate reducing agents such as borane complexes, for example borane-dimethyl sulfide ($[CH_3]_2S—BH_3$), aluminum hydrides or a lithium aluminum hydride complex in an inert organic solvent, at a temperature of between 0° C. and the reflux temperature of the reaction mixture, according to the customary techniques.

The expression "inert organic solvent" is understood to mean a solvent which does not interfere with the reaction. Such solvents are for example ethers, such as diethyl ether, tetrahydrofuran (THF), dioxane or 1,2-dimethoxyethane.

According to a preferred mode of operation, the procedure is carried out with the borane-dimethyl sulfide used in excess in relation to the starting compound (II), at the reflux temperature, optionally under an inert atmosphere. The reduction is normally complete after a few hours.

The dehydration of step (c) is easily carried out, for example, using an acetic acid/sulfuric acid mixture, at a temperature of between room temperature and the reflux temperature of the solvent used.

According to a preferred method, the reaction of step (c) is carried out in an acetic acid/sulfuric acid mixture in a 3/1 ratio by volume, by heating at the temperature of about 80-100° C. for 1 to 3 hours.

The desired compound is isolated according to conventional techniques in the form of a free base or of one of its salts. The free base may be converted to one of its salts by mere salification in an organic solvent such as an alcohol, preferably ethanol or 2-propanol, an ether such as 1,2-dimethoxyethane, ethyl acetate, acetone or a hydrocarbon such as hexane.

The compound of formula (I) obtained is optionally converted to one of its N-oxide derivatives.

The compounds of formula (I) bearing an N-oxide group on the nitrogen atom of the tetrahydropyridine can be prepared by oxidation of the corresponding compound of formula (I). In this case, the compound of formula (I) is subjected to an oxidation reaction according to conventional methods, for example to a reaction with m-chloroperbenzoic acid in a suitable solvent, and isolated according to the usual techniques well known to persons skilled in the art.

The compounds of formula (I) can also be prepared by a condensation reaction from a tetrahydropyridine of formula (VI):

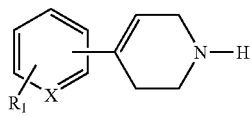

in which X and $R_1$ are as defined above, with a compound of formula (VII):

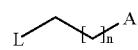

in which n and A are as defined above, and L is a leaving group, isolation of the compound of formula (I) thus obtained and optional conversion to one of its salts or solvates.

As leaving group "L", it is possible for example to use a halogen group, or any other group suitable for condensation with the compound of formula (VI).

The condensation reaction is carried out by mixing the starting compounds (VI) and (VII) in an organic solvent such as an alcohol such as for example methanol or butanol, in the presence of a base such as for example alkali metal carbonates, at a temperature of between room temperature and the reflux temperature of the chosen solvent, according to conventional methods.

The starting compounds of formula (II) are known or they can be prepared in a similar manner to the known compounds.

The compounds of formula (III°)

in which A° is a group of formula (a), (c) or (d) as defined above, n is an integer from 1 to 5 and m is 1 or 2, and their salts or solvates are novel compounds and constitute a subsequent aspect of the present invention.

When A is a group (a), these novel compounds are represented by formula (III')

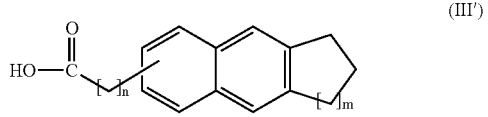

where n and m are as defined above, and may be synthesized by a method which involves:

(i) reacting compound (VIII) below (VIII)

where m is 1 or 2, with a dialkyl carbonate in the presence of a strong base such as an alkali metal hydride, (ii) reacting the compound of formula (IX) thus obtained (IX)

with a Hal-(CH$_2$)$_n$—COOAlk derivative in which n is as defined above, Alk is an alkyl group and Hal is a halogen atom, in the presence of a strong base such as an alkali metal hydride, (iii) hydrolyzing and decarboxylating the compound (X) thus obtained

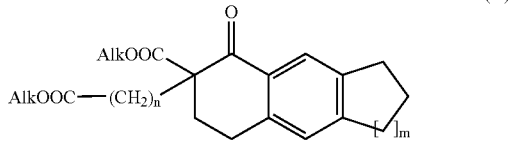

by heating in the presence of a base, such as sodium hydroxide, (iv) reducing the ketone of formula (XI) thus obtained (XI)

(v) aromatizing the compound of formula (XII) thus obtained (XII)

for example by oxidation with Pd/C at high temperature, in a solvent such as Decalin, obtaining the compound of formula (III') which is isolated according to conventional methods and optionally converted to one of its salts.

When A is a group (c), these novel compounds are represented by formula (III")

(III")

where n and m are as defined above.

When n is 0, these compounds may be synthesized according to a method which involves:

(vi) reacting the compound of formula (XIII)

(XIII)

with polyphosphoric acid (PPA) and reducing the 9-oxofluorene derivative thus obtained, obtaining the compound of formula (III") where n is 0; and when n is 1, (vii) esterifying and reducing the fluorenecarboxylic acid (XIV) thus obtained:

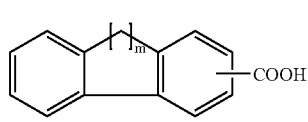
(XIV)

for example by reaction with methanol in the presence of hydrochloric acid followed by reduction with LiAlH$_4$ (viii) converting the alcohol of formula (XV) thus obtained

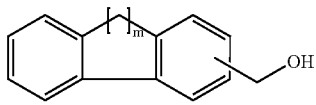
(XV)

to a cyano derivative, for example by preparation of the corresponding chloride and reaction with KCN;

(ix) and hydrolyzing this cyano derivative of formula (XVI)

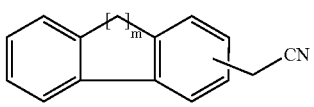
(XVI)

for example in an acid medium, obtaining the compound of formula (III″) where n is 1, which is isolated according to conventional methods and optionally converted to one of its salts.

If it is desired to prepare the compounds of formula (III″) where n is >1, it is sufficient to repeat the passages (vii)-(ix), although other known methods of synthesis may be used to extend the alkyl chain.

When A is a group (d), these novel compounds are represented by formula (III‴)

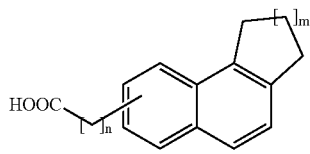
(III‴)

where n and m are as defined above.

The compounds of formula (III‴) where n is 0 or 1, may be synthesized according to a method which involves:

(x) reacting the compound of formula (XVII)

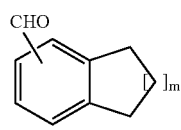
(XVII)

with (1-cyano-3,3-diethoxypropyl)diethyl phosphonate;

(xi) cyclizing the compound of formula (XVIII) thus obtained:

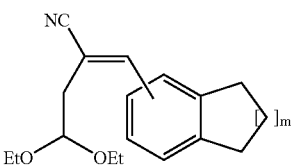
(XVIII)

for example in the presence of SnCl$_4$, and (xii) either hydrolyzing the cyano derivative of formula (XIX)

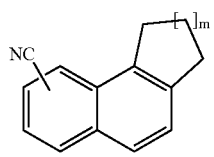
(XIX)

obtaining the compound of formula (III‴) where n is 0, (xiii) or, when n is 1, converting the derivative of formula (XIX) to a ketone of formula (XX)

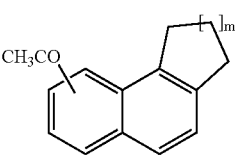
(XX)

for example by a Grignard reaction with CH$_3$MgI; and (xiv) converting the ketone (XX) to the corresponding acid of formula (III‴) where n is 1.

If it is desired to prepare the compounds of formula (III‴) where n is >1, it is sufficient to repeat the passages (vii)-(ix) above starting with the acid of formula (III‴) as obtained in the passage (xiv), or to use other methods of synthesis known to extend the alkyl chain.

When the cyclization of the passage (xi) is carried out starting with a beta-aldehyde, it is possible to obtain two derivatives of formula (XIX), because the formation of the aromatic ring may be achieved by cyclization on one of the two adjacent positions. In this case, the isomers thus formed should be separated, for example by means of chromatography on a silica gel column, and proceeding using the desired isomer.

The reactions described above are in general well known to persons skilled in the art. Detailed examples of such methods are in any case reported in the experimental section.

The compounds of the invention have advantageous properties with respect to the inhibition of TNF-α.

These properties were demonstrated with the aid of a test aimed at measuring the effect of molecules on the synthesis of TNF-α induced in Balb/c mice by lipopolysaccharide (LPS) from *Escherichia Coli* (055:B5, Sigma, St. Louis, Mo.).

The test products are administered orally to groups of 5 female 7- to 8-week old Balb/c mice (Charles River, France). One hour later, the LPS is administered intravenously (10 μg/mouse). The blood of each animal is taken 1.5 hours after the administration of the LPS. The samples are centrifuged and the plasma is recovered and frozen at −80° C. The TNF-α is measured using commercial kits (R and D, Abingdon, UK).

In this test, representative compounds of the invention were found to be very active, by inhibiting the synthesis of TNF-α even at very low doses.

By virtue of this activity and their low toxicity, the compounds of formula (I) and their salts or solvates can be used in the treatment of diseases linked to immune and inflammatory disorders or as analgesics. In particular, the compounds of formula (I) can be used for treating atherosclerosis, autoimmune diseases, diseases entailing demyelinization of the neurons (such as multiple sclerosis), asthma, rheumatoid arthritis, fibrotic diseases, pulmonary idiopathic fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, disseminated lupus erythematosus, hemodynamic shock, ischemic pathologies (myocardial infarction, myocardial ischemia, coronary vasospasm, angina pectoris, cardiac insufficiency, heart attack), post-ischemic reinfusion attacks, malaria, mycobacterial infections, meningitis, leprosy, viral infections (HIV, cytomegalovirus, herpesvirus), opportunistic infections associated with AIDS, tuberculosis, psoriasis, atopic dermatitis and contact dermatitis, diabetes, cachexia, cancer and radiation-mediated damage.

The compounds of formula (I) and the pharmaceutically acceptable salts and solvates thereof are preferably administered orally.

In the pharmaceutical compositions of the present invention for oral use, the active principle can be administered in unit administration forms, as a mixture with conventional pharmaceutical supports, to animals and human beings for the treatment of the abovementioned complaints. The appropriate unit administration forms comprise, for example, tablets, which may be splittable, gel capsules, powders, granules and oral solutions or suspensions.

When a solid composition in the form of tablets is prepared, the main active ingredient is mixed with a pharmaceutical vehicle such as gelatin, starch, lactose, magnesium stearate, talc, gum arabic or the like. The tablets can be coated with sucrose or other suitable materials or alternatively they can be treated such that they have sustained or delayed activity and such that they release a predetermined amount of active principle continuously.

A preparation in the form of gel capsules is obtained by mixing the active ingredient with a diluent and pouring the mixture obtained into soft or hard gel capsules.

A preparation in the form of syrup or elixir can contain the active ingredient together with a sweetener, preferably a calorie-free sweetener, methylparaben and propyl paraben as antiseptic agents, as well as a flavoring and a suitable colorant.

The water-dispersible powders or granules can contain the active ingredient as a mixture with dispersants or wetting agents, or suspending agents, such as polyvinylpyrrolidone, as well as with sweeteners or flavour enhancers.

The active principle can also be formulated in the form of microcapsules, optionally with one or more supports or additives.

In the pharmaceutical compositions according to the present invention, the active principle can also be in the form of an inclusion complex in cyclodextrins, or ethers or esters thereof.

The amount of active principle to be administered depends, as always, on the degree of progress of the disease as well as the age and weight of the patient. Nevertheless, the unit doses generally comprise from 0.001 mg to 100 mg, better still from 0.01 mg to 50 mg and preferably from 0.1 mg to 20 mg of active principle, advantageously from 0.5 mg to 10 mg.

According to another of its aspects, the present invention relates to a combination comprising a compound of formula (I) or one of its pharmaceutically acceptable salts or solvates, and at least one compound chosen from immunosuppressants, such as interferon beta-1b; adrenocorticotropic hormone; glucocorticoids such as prednisone or methylprednisolone; interleukin-1 inhibitors.

More particularly, the invention relates to a combination comprising a compound of formula (I), or one of its pharmaceutically acceptable salts or solvates, and at least one compound chosen from roquinimex (1,2-dihydro-4-hydroxy-N,1-dimethyl-2-oxo-3-quinolinecarboxanilide), myloran (product from the company Autoimmune containing bovine myelin), antegren (monoclonal human antibody from the companies Elan/Athena Neurosciences) and recombinant interferon beta-1b.

Other possible combinations are those consisting of a compound of formula (I), or one of its pharmaceutically acceptable salts or solvates, and a potassium-channel blocker such as, for example, fampridine (4-aminopyridine).

According to another of its aspects, the invention relates to a method for treating diseases linked to immune and inflammatory disorders as well as in the treatment of pain, in particular atherosclerosis, autoimmune diseases, diseases entailing demyelinization of the neurons (such as multiple sclerosis), asthma, rheumatoid arthritis, fibrotic diseases, pulmonary idiopathic fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, disseminated lupus erythematosus, hemodynamic shock, ischemic pathologies (myocardial infarction, myocardial ischemia, coronary vasospasm, angina pectoris, cardiac insufficiency, heart attack), post-ischemic reinfusion attacks, malaria, mycobacterial infections, meningitis, leprosy, viral infections (HIV, cytomegalovirus, herpesvirus), opportunistic infections associated with AIDS, tuberculosis, psoriasis, atopic dermatitis and contact dermatitis, diabetes, cachexia, cancer and radiation-mediated damage, comprising the administration of a compound of formula (I) or a pharmaceutically acceptable salt or solvate thereof, alone or in combination with other active principles.

EXAMPLES

The examples which follow illustrate the invention.

Preparation 1

1,2,3,6,7,8-Hexahydro-5H-cyclopenta[b]naphthalen-5-one

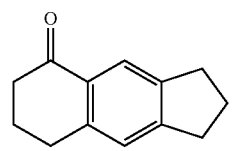

A suspension of 61 g (0.457 mol) of anhydrous AlCl₃ in 188 ml of a dichloromethane/nitromethane=8/1 mixture is cooled to 0-5° C. and 22.15 g of indan and, in portions, 22.5 g (0.225 mol) of succinic anhydride are added thereto. After one hour at 0° C., the medium is poured into a water/ice mixture, hydrochloric acid at 37% is added until a clear solution is obtained. The medium is extracted with ethyl acetate, washed with water, the organic phase is dried and the solvent is evaporated off under reduced pressure. A white solid is obtained which is dissolved in 500 ml of dioxane. 4.6 ml of sulfuric acid at 98% in 50 ml of ethanol and 3.6 g of 10% Pd/C are added thereto. After 5 hours under a hydrogen atmosphere, the catalyst is filtered off, the solvent is evaporated off, the residue is taken up in water and the medium is extracted with ethyl acetate. The product obtained is dissolved in 20 ml of methanol and 8 ml of a 1 N aqueous sodium hydroxide solution are added thereto and the medium is stirred at room temperature for 2 hours. The solvent is evaporated off, water is added, the medium is brought to an acidic pH, it is extracted and a white solid is isolated. 38.7 g of this product are dissolved in 1000 ml of anhydrous methylene chloride under a nitrogen atmosphere; the medium is cooled to 0° C. and 47 g (0.225 mol) of PCl₅ are carefully added thereto, the medium is stirred at 0° C. for two hours and 121.8 g (0.467 mol) of SnCl₄ are slowly added thereto and, after 10 minutes, the medium is allowed to heat up to room temperature. After two hours at room temperature, the medium is poured into a water/ice mixture, extracted with methylene chloride and an oil is isolated which is then purified by chromatography on a silica gel column, eluting with a cyclohexane/ethyl acetate=8/2 mixture. 6.0 g of the title compound are obtained.

Preparation 2

2,3-Dihydro-1H-cyclopenta[b]naphthalen-6-ylacetic acid

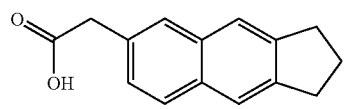

The procedure being carried out under a nitrogen stream, 3 g of sodium hydride at 80% (0.075 mol) are mixed in 845 ml of tetrahydrofuran and 0.7 g (0.0375 mol) of the product of Preparation 1, dissolved in 45 ml of tetrahydrofuran, is added thereto. After 1 hour under reflux, 9 ml (0.075 mol) of diethyl carbonate in 45 ml of tetrahydrofuran are added and the medium is kept stirring under reflux for 5 hours. The mixture is cooled and a saturated aqueous ammonium chloride solution and water are added thereto until complete dissolution is obtained and the medium is extracted with ethyl acetate. The medium is washed with water, the organic phase is dried and the solvent is evaporated off under reduced pressure. The oil obtained is dissolved in 60 ml of tetrahydrofuran and this solution is added, at room temperature and under a nitrogen atmosphere, to a suspension of sodium hydride at 80% (1.6 g; 0.41 mol) in 30 ml of tetrahydrofuran. The medium is stirred for 30 minutes and 8.8 ml of ethyl bromoacetate (0.08 mol) are added thereto, and the medium is stirred at room temperature for 5 hours. Ammonium chloride is added and the medium is extracted with methylene chloride. The medium is washed with water, the organic phase is dried and the solvent is evaporated off under reduced pressure. The oil thus obtained is dissolved in 600 ml of a 0.5 N aqueous-alcoholic solution of sodium hydroxide (EtOH/H₂O ratio=2/1). The medium is heated at about 40° C. until complete conversion of the product to its sodium salt is obtained (formation of a product with the base in the thin-layer chromatography trial, eluting with an ethyl acetate/hexane=3/7 mixture. After about 8 hours, half of the solvent is evaporated off under reduced pressure, the medium is acidified with 15 ml of 1 N hydrochloric acid and heated at 50° C. for about 45 minutes. The medium is extracted with ethyl acetate, the organic phase is dried and the solvent is evaporated off under reduced pressure. The product obtained is dissolved in 60 ml of acetic acid and 4.5 ml of sulfuric acid at 98%, diluted in 9 ml of acetic acid, and 1 g of 10% Pd/C are added thereto; the medium is then hydrogenated for 8 hours. Half of the solvent is evaporated off, the catalyst is filtered off, water is added and the medium is extracted with ethyl acetate, the organic phase is dried and the solvent is evaporated off. The product thus obtained is dissolved in 100 ml of methanol, 200 mg of para-toluenesulfonic acid are added thereto and the medium is heated under reflux for 4 hours. The solvent is partially evaporated off and 50 ml of a 5% aqueous sodium bicarbonate solution are added thereto and the medium is extracted with diethyl ether, the medium is washed with water and with brine. The organic phase is dried, and the solvent is evaporated off under reduced pressure. The product thus obtained is dissolved in Decalin (20 ml), 1.4 g of 10% Pd/C are added thereto and the medium is heated at 200° C. for 48 hours. The catalyst is filtered off, the solvent is evaporated off and the crude reaction product is purified by chromatography on a silica gel column, eluting with a cyclohexane/ethyl acetate=9/1 mixture. 750 mg of the product thus obtained are dissolved in 30 ml of ethanol, 20 ml of 1 N NaOH are added thereto and the medium is heated at 50° C. for 4 hours. The ethanol is evaporated off and the medium is acidified with 1 N HCl. A white solid is obtained.

m.p. 185-188° C.

Preparation 3

5-(2-Bromoethyl)indan 2 ml (0.016 mol) of indan in 33 ml of methylene chloride and 1.6 ml (0.019 mol) of bromoacetyl bromide are mixed at 0° C. 2.27 g (0.017 mol) of AlCl₃ are slowly added and the medium is allowed to return to room temperature and stirred for 2 hours. The mixture is poured into water/ice and extracted with methylene chloride. The organic phase is dried, filtered and the solvent is evaporated off under reduced pressure. The crude reaction product is crystallized from hexane. A white solid is separated (m.p. 57.8-58.1° C.) corresponding to the acylation product. 1.67 g (7 mmol) of this product are dissolved in 3.9 ml of triethylsilane and 3.9 ml of trifluoroacetic acid and the medium is heated at 80° C. for two hours. The medium is poured into an ice/NaOH mixture and extracted with ethyl acetate. The title compound is obtained.

Preparation 4

2-(2-Bromoethyl)-5,6,7,8-tetrahydronaphthalene

By carrying out the procedure as described in Preparation 3 but using Tetralin instead of indan, the title compound is obtained.

Preparation 5

5-(3-Bromopropyl)indan

By carrying out the procedure as described in Preparation 3 but using bromopropionyl bromide instead of bromoacetyl bromide, the title compound is obtained.

Preparation 6

5-(3-Bromobutyl)indan

By carrying out the procedure as described in Preparation 3 but using bromobutanoyl bromide instead of bromoacetyl bromide, the title compound is obtained.

Preparation 7

2-(2-Bromoethyl)fluorene

By carrying out the procedure as described in Preparation 3 but using fluorine instead of indan, the title compound is obtained.

Preparation 8

2-(2-Bromoethyl)-9,10-dihydrophenanthrene

By carrying out the procedure as described in Preparation 3 but using 9,10-dihydrophenanthrene instead of indan, the title compound is obtained.

Preparation 9

3-Fluorenylacetic acid

9a) 9-Oxofluoren-3-ylcarboxylic acid

A mixture of 0.45 g (0.00186 mol) of 2,5-biphenyldicarboxylic acid and 13.9 g of polyphosphoric acid (PPA) is heated to 200° C. After one hour, the medium is cooled to 100° C. and ice is added thereto until a volume of about 100 ml is obtained. The medium is filtered and a solution of 0.5 g of NaOH in 90 ml of water is added to the precipitate and the medium is stirred for one hour at 60° C. The medium is acidified with hydrochloric acid and extracted with ethyl acetate. The organic phase is dried, filtered and the solvent is evaporated off under reduced pressure. 0.31 g of the title product is obtained in the form of a light brown solid.

9b) Fluoren-3-ylcarboxylic acid 0.27 g (0.0012 mol) of the product of the preceding step is dissolved in 2.5 ml of ethylene glycol and 0.1 g of NaOH and 0.25 ml of hydrazine at 98% (d=1.03) are added thereto. The medium is heated under reflux for 1.5 hours, it is allowed to return to room temperature, 70 ml of water are added and the medium is acidified to pH=6 with hydrochloric acid. The medium is extracted with ethyl acetate, the organic phase is dried, filtered and the solvent is evaporated off under reduced pressure. 0.4 g of the title product is thus obtained in the form of a yellow solid.

9c) Methyl ester of fluoren-3-ylcarboxylic acid

The ester of the product of the preceding step is prepared with the aid of methanol in hydrochloric acid. The solution is brought to a basic pH and extracted with ethyl acetate, thus obtaining the title product in the form of an oil.

9d) 3-Hydroxymethylfluorene

A mixture of 0.68 g of $LiAlH_4$ in 7 ml of anhydrous ethyl ether is cooled to 0° C. and under a nitrogen stream, and a solution of 3.4 g (0.0152) of the product of the preceding step in 27 ml of anhydrous ethyl ether are added thereto dropwise and the medium is stirred overnight. A water/ice mixture is then added, the medium is extracted with ethyl acetate, the organic phase is dried, filtered and the solvent is evaporated off under reduced pressure. 3 g of the crude product are thus obtained, which product is purified by chromatography on a silica gel column, eluting with a cyclohexane/ethyl acetate 7/3 mixture. 1.33 g of the title product are thus obtained in the form of a white solid.

9e) 3-Chloromethylfluorene

A solution of 35 mg (0.178 mmol) of the product of the preceding step in 0.5 ml of methylene chloride is cooled to 0° C. and 0.13 ml of thionyl chloride (1.178 mmol) is added thereto dropwise. The mixture is stirred for three hours at room temperature and a mixture of water and sodium bicarbonate is added thereto to pH 8. The medium is extracted with methylene chloride, the organic phase is dried, filtered and the solvent is evaporated off under reduced pressure. 20 mg of the title product are thus obtained in the form of a yellow oil.

9f) 3-Cyanomethylfluorene 1.3 g (0.00605 g) of the product of the preceding step are dissolved in 32 ml of DMSO and 0.44 g (0.00666 mol) of KCN is added thereto. The medium is heated at 80° C. for 3 hours, a water/ice mixture is added thereto and the medium is extracted with ethyl acetate. The organic phase is dried, filtered and the solvent is evaporated off under reduced pressure. The crude product is purified by flash chromatography, eluting with a cyclohexane/ethyl acetate 8/2 mixture. 250 mg of the title product are thus obtained.

9g) 3-Fluorenylacetic acid

The cyano derivative of the preceding step is hydrolyzed with the aid of 6 N hydrochloric acid while heating under reflux. A water/ice mixture is added and the medium is extracted with ethyl acetate. The organic phase is dried, filtered and the solvent evaporated off under reduced pressure. 0.22 g of the title product is thus obtained in the form of a solid.

m.p.: 166-168° C.

Preparation 10

2,3-Dihydro-1H-cyclopenta[a]naphthalen-8-ylacetic acid

10a) 4,4-Diethoxy-2-indan-4-ylmethylenebutyronitrile 0.23 g (0.0092 mol) of NaH at 60% in 20 ml of anhydrous THF is cooled at 0° C. under a nitrogen stream and a solution of 2.26 g (0.0085 mol) of a diethyl ester of (1-cyano-3,3-diethoxypropyl)phosphonic acid in 16 ml of THF is added thereto. After 30 minutes, the mixture becomes clear and a solution of 1.1 g (0.0075 mol) of 2,3-dihydro-1H-inden-8- ylbenzaldehyde in 16 ml of THF is then added thereto dropwise. The medium is stirred for one hour at 0° C. and a water/ice mixture is added. The medium is extracted with methylene chloride, the organic phase is washed with an NaOH/water solution, the organic phase is dried, filtered and the solvent is evaporated off under reduced pressure. 2.49 g of the crude product are thus obtained in the form of an orange-colored oil which is purified by flash chromatography, eluting with a cyclohexane/ethyl acetate 95/5 mixture. The title product is thus obtained.

10b) 8-Cyano-2,3-dihydro-1H-cyclopenta[a]naphthalene

A mixture of 0.56 g (0.0021 mol) of the product of the preceding step in 14 ml of methylene chloride is cooled to 0° C. and 152 ml (0.0013 mol) of $SnCl_4$ (d=2.226) are added thereto dropwise. The medium is stirred at room temperature for 4 hours, sodium bicarbonate at 10% is then added thereto and the medium is extracted with methylene chloride. The organic phase is dried, filtered and the solvent is evaporated off under reduced pressure. 0.43 g of the title product is thus obtained in the form of a light yellow solid.

10c) 8-Methylcarbonyl-2,3-dihydro-1H-cyclopenta[a]naphthalene 0.5 g (0.0025 mol) of the product of the preceding step is dissolved in 20 ml of anhydrous toluene and 1.6 ml (0.005 mol) of 3 M methylmagnesium iodide are added thereto dropwise and under a nitrogen stream. The medium is stirred overnight at room temperature, and water and hydrochloric acid are then added thereto. The medium is stirred for 15 minutes, brought to a basic pH with a 5 M NaOH solution and extracted with ethyl acetate. The organic phase is washed, it is dried, filtered and the solvent is evaporated off under reduced pressure. 0.69 g of the crude product is thus obtained, which product is purified by flash chromatography, eluting with a hexane/diethyl ether 95/5 mixture. 0.35 g of the title product is thus obtained.

10d) 8-(Morpholinothiocarbonyl)-2,3-dihydro-1H-cyclopenta[a]naphthalene 0.35 g (0.0016 mol) of the product of the preceding step is dissolved in 0.35 ml (0.0016 mmol) of morpholine (d=0.999) and 0.54 g (0.0020) of sulfur and a crystal of para-toluenesulfonic acid (PTSA) are added thereto. The medium is heated under reflux for 6 hours and methanol is then added. The medium is stirred at room temperature overnight. The solvent is removed under reduced pressure and 2.5 g of the crude product are thus obtained, which product is purified by flash chromatography, eluting with a cyclohexane/ethyl acetate 9/1 mixture. 0.16 g of the title product is thus obtained.

10e) 2,3-Dihydro-1H-cyclopenta[a]naphthalen-8-ylacetic acid 0.16 g (0.0005 mol) of the product of the preceding step is dissolved in 7.6 ml of a 1:1 methanol/water solution and 0.02 g of solid NaH is added thereto. The medium is heated under reflux for 6 hours, the solvent is then removed under reduced pressure, the residue is taken up in a water and ethyl acetate mixture, the organic phase is removed, the aqueous phase is acidified and extracted with methylene chloride. The organic phase is dried, filtered and the solvent evaporated off under reduced pressure. 20 mg of the title product are thus obtained.

Preparation 11

5,6,7,8-Tetrahydrophenanthren-3-ylacetic acid

By following the procedure described in Preparation 10 but using 5,6,7,8-tetrahydronaphthalen-1-ylbenzaldehyde instead of 2,3-dihydro-1H-inden-7-ylbenzaldehyde, the title product is obtained.

Preparation 12

5,6,7,8-Tetrahydroanthren-2-ylacetic acid

By following the procedure described in Preparation 10 but using 5,6,7,8-tetrahydronaphthalen-2-ylbenzaldehyde instead of 2,3-dihydro-1H-inden-7-ylbenzaldehyde, the title product is obtained.

Example 1

1-[2-(2,3-Dihydro-1H-cyclopenta[b]naphthalen-6-yl)ethyl]-4-[3-trifluoromethylphenyl]-1,2,3,6-tetrahydropyridine and its hydrochloride

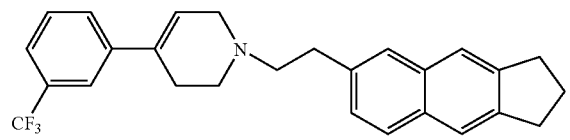

1a) 1-[4-Hydroxy-4-(3-trifluoromethylphenyl)-1-piperidinyl]-2-(2,3-dihydro-1H-cyclopenta[b]naphthalen-6-yl)-1-ethanone 400 mg (1.76 mol) of the product of Preparation 2 are dissolved under a nitrogen atmosphere in 10 ml of anhydrous methylene chloride and 430 mg (1.76 mol) of 4-hydroxy-4-(3-trifluoromethylphenyl)piperidine, 0.79 g (1.76 mol) of BOP and 0.73 ml of triethylamine are added thereto and the medium is stirred at room temperature for 3 hours. 40 ml of ethyl acetate are added, the medium is washed with a 1 N hydrochloric acid solution, then with a 1 N sodium hydroxide solution, and then with water. The organic phase is dried over sodium sulfate and the solvent is evaporated off. 0.8 g of the title compound is obtained in the form of an oil.

1b) 1-[2-(2,3-Dihydro-1H-cyclopenta[b]naphthalen-6-yl)ethyl]-4-hydroxy-4-(3-trifluoromethylphenyl)piperidine The product obtained in Example 1a is dissolved in 7 ml of anhydrous THF, the medium is heated under reflux and 0.5 ml of borane-dimethyl sulfide is added thereto and the medium is heated under reflux for 4 hours. The medium is cooled to 0-5° C. and 7 ml of methanol are carefully added thereto. After 5 minutes, the medium is heated under reflux for 30 minutes, the solvent is evaporated off, the residue is taken up in the water/ammonia=1/1 mixture, the medium is extracted with ethyl acetate, the two phases are separated and the organic phase is washed with water. The medium is dried over sodium sulfate and the solvent is evaporated off under reduced pressure. The crude crystallization product is purified in 2-propyl ether. 0.37 g of the title product is obtained.

m.p. 154-156° C.

1c) 1-[2-(2,3-Dihydro-1H-cyclopenta[b]naphthalen-6-yl)ethyl]-(4-(3-trifluoromethylphenyl)-1,2,3,6-tetrahydropyridine and its hydrochloride 350 mg (0.8 mmol) of the product of the preceding step are dissolved in 10 ml of acetic acid, 1 ml of sulfuric acid at 96% is added thereto and the medium is heated at 80° C. for 2 hours. The medium is cooled, concentrated NH$_4$OH is added thereto and the medium is extracted with ethyl acetate. The medium is washed with water, dried and evaporated under reduced pressure. The title compound is obtained. The hydrochloride is prepared with the aid of a solution of 2-propanol saturated with hydrochloric acid.

m.p. (hydrochloride) 264-266° C.

Example 2

1-[2-(2,3-Dihydro-1H-inden-5-yl)ethyl]-4-[3-trifluoromethylphenyl]-1,2,3,6-tetrahydropyridine and its hydrochloride

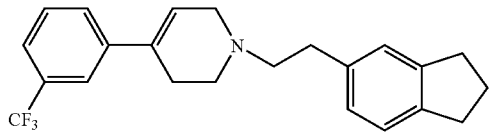

The product obtained in Preparation 3 is dissolved in 17 ml of butanol. 0.84 g (3.2 mol) of 4-(3-trifluoromethylphenyl)-1,2,3,6-tetrahydropyridine and 0.9 g (6.5 mmol) of potassium carbonate are added thereto and the medium is heated under reflux for 5 hours. The solvent is evaporated off and the residue is washed with water. It is extracted with methylene chloride, the organic phase is dried and the solvent is evaporated off under reduced pressure. The residue is purified on a silica gel column, eluting with a cyclohexane/ethyl acetate=8/2 mixture. The title compound is obtained. The hydrochloride is prepared with the aid of 2-propanol saturated with hydrochloric acid.

m.p. (hydrochloride) 252-255° C.

Example 3

1-[2-(5,6,7,8-Tetrahydronaphthalen-2-yl)ethyl]-4-[3-trifluoromethylphenyl]-1,2,3,6-tetrahydropyridine and its hydrochloride

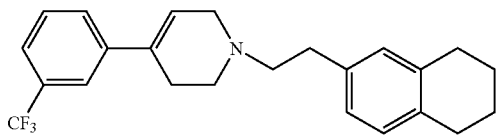

By carrying out the procedure as described in Example 2 but using the product of Preparation 4 instead of the product of Preparation 3, the title compounds are obtained.

m.p. (hydrochloride): 263-267° C.

Example 4

1-[2-(2,3-Dihydro-1H-cyclopenta[b]naphthalen-6-yl)ethyl]-4-(6-chloropyrid-2-yl)-1,2,3,6-tetrahydropyridine and its hydrochloride

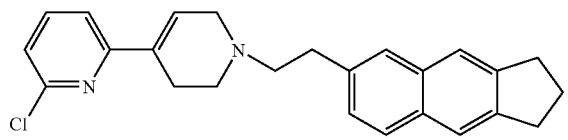

By carrying out the procedure as described in Example 1 but using 4-(6-chloropyrid-2-yl)-1,2,3,6-tetrahydropyridine instead of 4-(3-trifluoromethylphenyl)-1,2,3,6-tetrahydropyridine, the title compounds are obtained.

m.p. (hydrochloride): 254-258° C.

Example 5

1-[2-(2,3-Dihydro-1H-cyclopenta[b]naphthalen-6-yl)ethyl]-4-(6-trifluoromethylpyrid-2-yl)-1,2,3,6-tetrahydropyridine and its hydrochloride

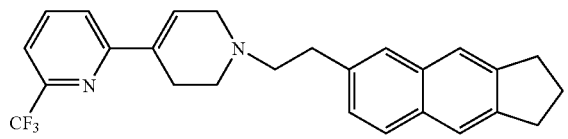

By carrying out the procedure as described in Example 1 but using 4-(6-trifluoromethylpyrid-2-yl)-1,2,3,6-tetrahydropyridine instead of 4-(3-trifluoromethylphenyl)-1,2,3,6-tetrahydropyridine, the title compounds are obtained.

m.p. (hydrochloride): 264-267° C.

Example 6

1-[3-(2,3-Dihydro-1H-inden-5-yl)propyl]-4-(3-trifluoromethylphenyl)-1,2,3,6-tetrahydropyridine and its hydrochloride

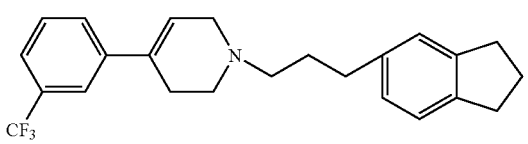

By carrying out the procedure as described in Example 2 but using the product of Preparation 5 instead of the product of Preparation 3, the title compounds are obtained.

m.p. (hydrochloride): 192-195° C.

Example 7

1-[4-(2,3-Dihydro-1H-inden-5-yl)butyl]-4-(3-trifluoromethylphenyl)-1,2,3,6-tetrahydropyridine and its hydrochloride

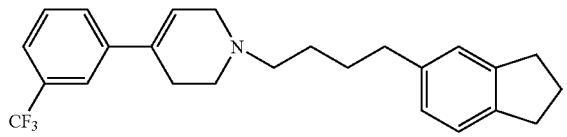

By carrying out the procedure as described in Example 2 but using the product of Preparation 6 instead of the product of Preparation 3, the title compounds are obtained.

m.p. (hydrochloride): 198-200° C.

Example 8

1-[2-(Fluoren-2-yl)ethyl]-4-(3-trifluoromethylphenyl)-1,2,3,6-tetrahydropyridine and its hydrochloride

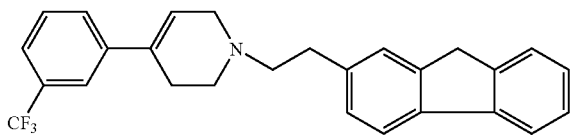

By carrying out the procedure as described in Example 2 but using the product of Preparation 7 instead of the product of Preparation 3, the title compounds are obtained.

m.p. (hydrochloride): 285-287° C.

Example 9

1-[2-(9,10-Dihydrophenanthren-2-yl)ethyl]-4-(3-trifluoromethylphenyl)-1,2,3,6-tetrahydropyridine and its hydrochloride

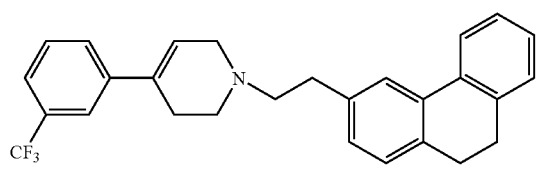

By carrying out the procedure as described in Example 2 but using the product of Preparation 8 instead of the product of Preparation 3, the title compounds are obtained.

m.p. (hydrochloride): 256-258° C.

Example 10

1-[2-(2,3-Dihydro-1H-cyclopenta[b]naphthalen-6-yl)ethyl]-(4-(3-trifluoromethylphenyl)-1,2,3,6-tetrahydropyridine 1-oxide

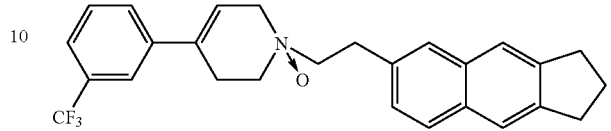

0.27 g of m-chloroperbenzoic acid is added to a solution of 0.47 g (1.1 mmol) of 1-[2-(2,3-dihydro-1H-cyclopenta[b]naphthalen-6-yl)ethyl]-4-(6-trifluoromethylpyrid-2-yl)-1,2,3,6-tetrahydropyridine in 40 ml of methylene chloride at the temperature of 0-5° C. The medium is kept stirring at 0-5° C. for two hours, washed with a saturated aqueous sodium bicarbonate solution and the two phases are separated. The organic phase is dried, filtered and evaporated under reduced pressure. The medium is purified by chromatography, eluting with a methanol/ethyl acetate=1/1 mixture and the title product is obtained.

m.p.: 116-117° C.

Example 11

1-[2-(Fluoren-3-yl)ethyl]-(4-(3-trifluoromethylphenyl)-1,2,3,6-tetrahydropyridine and its hydrochloride

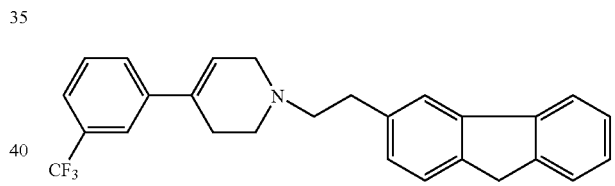

By carrying out the procedure as described in Example 1 but using the product of Preparation 9 instead of the product of Preparation 2, the title compounds are obtained.

m.p. (hydrochloride): 238-240° C.

Example 12

1-[2-(2,3-Dihydro-1H-cyclopenta[α]naphthalen-8-yl)ethyl]-4-(3-trifluoromethylphenyl)-1,2,3,6-tetrahydropyridine and its hydrochloride

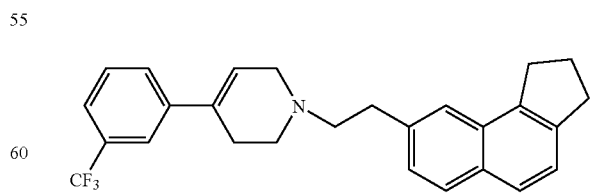

By carrying out the procedure as described in Example 1 but using the product of Preparation 10 instead of the product of Preparation 2, the title compounds are obtained.

m.p. (hydrochloride): 212-213° C.

Example 13

1-[2-(5,6,7,8-Tetrahydrophenanthren-3-yl)ethyl]-(4-(3-trifluoromethylphenyl)-1,2,3,6-tetrahydropyridine and its hydrochloride

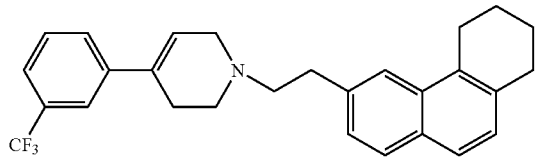

By carrying out the procedure as described in Example 1 but using the product of Preparation 11 instead of the product of Preparation 2, the title compounds are obtained.
m.p. (hydrochloride): 222-224° C.

Example 14

1-[2-(5,6,7,8-Tetrahydroanthracen-2-yl)ethyl]-(4-(3-trifluoromethylphenyl)-1,2,3,6-tetrahydropyridine and its hydrochloride

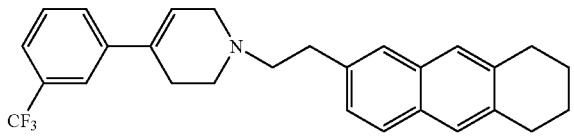

By carrying out the procedure as described in Example 1 but using the product of Preparation 12 instead of the product of Preparation 2, the title compounds are obtained.
m.p. (hydrochloride): 252-253° C.

We claim:

1. A compound of formula (III°)

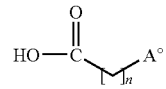

(III°)

Wherein:
A° is a group of formula (a) to (d):

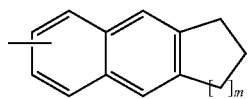

(a)

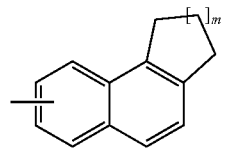

(d)

m is 1 or 2; and
n is an integer from 1 to 5;
or a salt thereof.

2. The compound according to claim 1, which is:
2,3-Dihydro-1H-cyclopenta[a]naphthalen-8-ylacetic acid;
5,6,7,8-Tetrahydrophenanthren-3-ylacetic acid; or
5,6,7,8-Tetrahydroanthren-2-ylacetic acid;
or a salt thereof.

* * * * *